United States Patent [19]

Green

[11] Patent Number: 4,753,912

[45] Date of Patent: Jun. 28, 1988

[54] NOVEL CATALYST AND REACTIONS EMPLOYING SAME

[75] Inventor: Michael J. Green, Hull, United Kingdom

[73] Assignee: BP Chemicals Limited, London, England

[21] Appl. No.: 606,716

[22] Filed: May 3, 1984

[30] Foreign Application Priority Data

May 10, 1983 [GB] United Kingdom ............... 8312781

[51] Int. Cl.$^4$ ............................................. B01J 31/00
[52] U.S. Cl. .................................. 502/167; 502/162; 568/8; 568/13; 568/15
[58] Field of Search ............... 568/8, 13, 15; 502/155, 502/162, 167

[56] References Cited

U.S. PATENT DOCUMENTS

| 3,948,980 | 4/1976 | Dettmeier et al. ............... 568/15 X |
| 4,007,229 | 2/1977 | Hechenbleikner ................... 568/15 |
| 4,315,867 | 2/1982 | Hänssle ............................. 568/8 X |

OTHER PUBLICATIONS

Kosolapoff et al., Organic Phosphorus Compounds, vol. 1, Wiley-Intersc., N.Y., pp. 127, 137, 139, 140, 142 to 144, 146 to 150, 152 to 154, 156, 158, 159, 162, 169 and 170, (1972).
Chemical Abstracts, V78, 123382u, (1973).
McClure, J. Org. Chem., vol. 56, No. 9, pp 3045 to 3048, (1970).

*Primary Examiner*—Paul F. Shaver
*Attorney, Agent, or Firm*—Brooks Haidt Haffner & Delahunty

[57] ABSTRACT

A novel catalyst comprises (i) an organophosphorus-containing compound, (ii) a compound, which is reactable in the Michael reaction, and contains both (a) a double or triple bond and (b) an electron withdrawing group and (iii) an alcohol or a mixture of an alcohol and a solvent. The novel catalyst may be generated from a novel catalyst precursor. The catalyst may be used to transesterify carboxylic or carbonic acid esters, to produce formate esters from alcohols and carbon monoxide and to produce formamides from amines and carbon monoxide.

8 Claims, No Drawings

NOVEL CATALYST AND REACTIONS EMPLOYING SAME

This invention relates to a novel catalyst precursor, a novel catalyst and to processes in which the catalyst is employed.

According to the present invention, there is provided a novel catalyst precursor which comprises (i) an organophosphorus-containing compound in which the phosphorus is trivalent and (ii) a compound, which is reactable with the organophosphorus-containing compound in the Michael reaction, and contains both (a) a double or triple bond and (b) an electron withdrawing group.

The catalyst precursor is converted into a novel catalyst by mixing the catalyst precursor with an alcohol or a mixture of an alcohol and a solvent.

Accordingly an embodiment of the present invention provides a novel catalyst which comprises (i) an organophosphorus-containing compound, (ii) a compound, which is reactable with the organophosphorus-containing compound in the Michael reaction, and contains both (a) a double or triple bond and (b) an electron withdrawing group and (iii) an alcohol or a mixture of an alcohol and a solvent.

Although the catalyst is conveniently prepared by adding the catalyst precursor to the alcohol or alcohol/solvent mixture, it will be obvious to the skilled man that the catalyst can be prepared by adding the components of the catalyst precursor directly to the alcohol or alcohol/solvent mixture without prior mixing.

The organophosphorus-containing compound is one in which the phosphorus is trivalent. Conveniently, the phosphorus compound is a mono-, di- or trialkylphosphine in which each of the alkyl groups contains from one to ten carbon atoms. The individual alkyl groups can all be the same or may be different. Examples of such phosphines are tributyl phosphine, trimethylphosphine, dibutylethylphosphine, dibutylphosphine, monopropylphosphine and the like. The phosphine may also be a mono-, di- or triarylphosphine or a mixed phosphine containing both alkyl and aryl groups. Examples of such phosphines are triphenylphosphine and dimethylphenylphosphine. Polydentate phosphorus compounds such as bis 1,2-diphenyl phosphino ethane can also be used.

The organophosphorus compounds described in the previous paragraph are either partially or completely soluble in the reaction mixture. However, it is possible, and in some cases convenient to use an organophosphorus compound which is chemically bonded to an insoluble solid support. Such supported organophosphorus compounds are able to function in the same way as those which are soluble but have the advantage that they are easily separated from the reaction products by simple filtration methods.

The supported organophosphorus compound conveniently comprises a trivalent organophosphorus compound of the formula

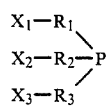

wherein $R_1$, $R_2$, and $R_3$ are independent divalent alkyl, aryl or cycloalkyl hydrocarbyl radicals. The remaining valences on $R_1$, $R_2$ and $R_3$ are bonded to $X_1$, $X_2$ and $X_3$ respectively. $X_1$, $X_2$ and $X_3$ may be either hydrogen or surface atoms of the insoluble solid support. In the latter case $X_1$, $X_2$ and $X_3$ have further valances which bond them to the bulk of the support. Examples of the divalent $R_1$, $R_2$ and $R_3$ groups are $-C_6H_4-$, $-(CH_2)_2-$ (n=0 to 10), $-CH_2-C_6H_4-CH_2-$ and the like.

The insoluble solid support may be organic for example a polymer such as polystyrene, or a polystyrene/divinylbenzene copolymer, as found in commercial resins, or can be inorganic for example a silica, diatomaceous earth, an aluminosilicate, a clay or a zeolite. The supported phosphorus catalyst may take a variety of physical forms e.g. powder, pellets, spheres or extrudate.

The compound (ii) containing the double or triple bond and electron withdrawing group can be of the formula:

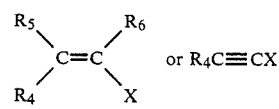

where X is an electron withdrawing group for example $-COOR$, $-COR$, $-CHO$, $-CON(R)_2$, or $-CN$ where R is alkyl or aryl and where $R_4$, $R_5$ and $R_6$ are hydrogen or monovalent hydrocarbyl groups. Examples of preferred compounds are ethyl acrylate, methyl methacrylate, methyl acrylate, acrylonitrile and acrolein.

The molar proportions of the two components of the catalyst precursor can be such as to provide from 10:1 to 1:10, preferably 2:1 to 1:2, atoms of phosphorus per double or triple bond.

The catalyst precursor is converted into a catalyst by addition to an alcohol or an alcohol/solvent mixture. Conveniently the alcohol is an aliphatic alcohol such as methanol, ethanol, propanol, or ethylene glycol of which methanol is preferred. The alcohol is present in amounts such that the molar ratio of phosphorus to alcohol is in the range 2:1 to 1:10,000 preferably 1:10 to 1:1000.

As regards solvent, this can be any organic liquid which is miscible with the alcohol and chemically inert under the conditions in which the catalyst is used.

The novel catalyst described herein has been shown to be useful for catalysing three reactions.

According to another aspect of the present invention, a process for the transesterification of a carboxylic or carbonic acid ester comprises contacting the ester with an alcohol under transesterification conditions in the presence of an effective amount of the catalyst precursor or catalyst described above.

The ester starting material can be an alkyl, aryl or aralkyl ester of a saturated or unsaturated aliphatic or aromatic carboxylic acid. Conveniently the ester is a $C_1$ to $C_{12}$ alkyl ester. The term alkyl ester is intended to include esters such as benzyl acetate.

Conveniently the alcohol is a $C_1$ to $C_{12}$ alcohol preferably a primary alcohol such as methanol, ethanol and the like.

The reaction can be conveniently effected at a temperature in the range 15° to 150° C. and at a pressure of from 1 to 150 bar. The amount of catalyst precursor or catalyst is preferably from 0.0001% to 5% by weight more preferably 0.01 to 1% by weight based on weight of reactants.

According to another aspect of the present invention a process for the carbonylation of an alcohol to a formate ester comprises contacting the alcohol with carbon monoxide under carbonylation conditions with an effective amount of the catalyst precursor or catalyst described above.

Conveniently the process is carried out under super-atmospheric pressure, for example, in the range 20 to 120 bar and at elevated temperature, for example in the range 40° to 150° C.

The alcohol is conveniently an alkanol but may be an aralkyl alcohol e.g. benzyl alcohol. The term alkyl in the present specification is therefore intended to include aralkyl.

Preferably the alcohol is a primary lower aliphatic alcohol, for example methanol, ethanol, n-propanol, or n-butanol.

Preferably the proportions of carbon monoxide and alcohol in the reaction zone are such that excess carbon monoxide is present over that required for conversion of the alcohol to the corresponding alkyl formate.

The amount of catalyst precursor or catalyst is preferably from 0.01 to 50% more preferably from 1 to 20% by weight based on weight of reactants.

According to a further aspect of the present invention a process for the carbonylation of ammonia or a primary or secondary amine to form a formamide comprises contacting the amine or ammonia with
(a) an alkyl formate or
(b) an alcohol and carbon monoxide
under carbonylation conditions in the presence of an effective amount of the catalyst precursor or catalyst described above.

The primary or secondary amine can be of the formula $R^1R^2NH$ where $R^1$ and $R^2$, which can be the same or different are hydrogen atoms or hydrocarbyl groups e.g. $C_1$ to $C_{10}$ alkyl groups.

Conveniently the alkyl formate is a $C_1$ to $C_{12}$ alkyl formate and the $R^1$ and $R^2$ groups are conveniently $C_1$ to $C_{12}$ hydrocarbyl groups. Conveniently the alcohol is a $C_1$ to $C_{12}$ alcohol preferably a primary or secondary alcohol.

Conveniently the alcohol is present in an amount from 5 to 95% by weight of the reaction mixture.

The term alkyl in the present specification is intended to include aralkyl for example benzyl.

The process is conveniently effected at a temperature in the range 20° to 150° C. and for example from 1 bar to 150 bar.

Convenient molar proportions of carbon monoxide to alcohol and carbon monoxide to amine are such that excess carbon monoxide is present over that required for complete conversion of the amine to the formamide.

It is possible, by adjustment of the reaction conditions, to produce not only the formamide but also varying amounts of an alkyl formate of formula $HCOOR^3$ where $R^3$ is a $C_1$ to $C_{12}$ alkyl (which $C_1$ to $C_{12}$ alkyl is the alkyl of the $C_1$ to $C_{12}$ alcohol).

The process of the present invention can employ ammonia or primary or secondary amines and is particularly suitable for preparing, formamide itself where $R^1R^2NH$ is ammonia, n-propylformamide where $R^1R^2NH$ is n-propylamine, dimethylformamide where $R^1R^2NH$ is dimethylamine and diethylformamide where $R^1R^2NH$ is diethylamine respectively.

The amount of catalyst precursor or catalyst is preferably from 0.01 to 50% more preferably from 1 to 20% by weight based on the weight of the reactants.

All three reactions may be carried out batchwise or continuously.

It will be obvious to those skilled in the art that when one of the reactants present in the reaction mixture is an alcohol, the catalyst precursor may be added directly to the reaction mixture and the catalyst generated in situ if convenient. Alternatively the catalyst may be prepared in an alcohol, which may be the same or different to the alcohol used in the reactions, and then added to the reaction mixture.

The invention is illustrated by the following examples.

EXAMPLE 1

Transesterification of ethyl acetate to methyl acetate

Ethyl acetate (2 g) was added to a solution containing 2 g of methanol, 0.04 g of tributyl phosphine, and 0.04 g of ethyl acrylate, and the resulting mixture was maintained at 24° C. for 2 h. Analysis of the liquid product showed an ethyl acetate conversion of 78% to methyl acetate.

EXAMPLE 2

Transesterification of ethyl acetate to methyl acetate

Example 1 was repeated in the presence of 0.008 g of tributylphosphine and 0.008 g of ethyl acrylate. Analysis of the liquid product showed an ethyl acetate conversion of 53% to methyl acetate.

EXAMPLE 3

Transesterification of ethyl formate to methyl formate

Example 1 was repeated except that 2 g of ethyl formate was used in place of ethyl acetate. Analysis of the liquid product showed an ethyl formate conversion of 77% to methyl formate.

EXAMPLE 4

Transesterification of ethyl propionate to methyl propionate

Example 1 was repeated except that 2 g of ethyl propionate was used in place of ethyl acetate. Analysis of the liquid product showed an ethyl propionate conversion of 78% to methyl propionate.

EXAMPLE 5

Transesterification of benzyl acetate to methyl acetate

Example 1 was repeated except that 2 g of benzyl acetate was used in place of ethyl acetate. Analysis of the liquid product showed a benzyl acetate conversion of 91% to methyl acetate.

EXAMPLE 6

Transesterification of ethyl benzoate to methyl benzoate

Example 1 was repeated except that 2 g of ethyl benzoate was used in place of ethyl acetate. Analysis of the liquid product showed an ethyl benzoate conversion of 36% to methyl benzoate. (After 24 hours the conversion was 83%).

EXAMPLE 7

Transesterification of ethyl acetate to methyl acetate

Example 1 was repeated except that 0.04 g of acrylamide was used in place of ethyl acrylate. Analysis of the liquid product showed an ethyl acetate conversion of 77% to methyl acetate.

EXAMPLE 8

Transesterification of ethyl acetate to methyl acetate

Example 1 was repeated except that 0.04 g of methyl propiolate was used in place of ethyl acrylate. Analysis of the liquid product showed an ethyl acetate conversion of 51% to methyl acetate.

EXAMPLE 9

Transesterification of ethyl acetate to methyl acetate

Example 1 was repeated except that 0.04 g of methyl vinyl ketone was used in place of ethyl acrylate. Analysis of the liquid product showed an ethyl acetate conversion of 78% to methyl acetate.

EXAMPLE 10

Transesterification of ethyl acetate to methyl acetate

Example 1 was repeated except that 0.04 g of acrylonitrile was used in place of ethyl acrylate. Analysis of the liquid product showed an ethyl acetate conversion of 79% of methyl acetate.

EXAMPLE 11

Transesterification of ethyl acetate to methyl acetate

Example 1 was repeated except that 0.04 g of ethyl crotonate was used in place of ethyl acrylate. Analysis of the liquid product showed an ethyl acetate conversion of 62% to methyl acetate.

EXAMPLE 12

Transesterification of ethyl acetate to methyl acetate

A solution containing 50 g of methanol, 0.5 g of tributyl phosphine, and 0.5 g of methyl acrylate was heated under reflux for 30 min to generate the catalyst. On cooling, 2 g of the solution was added to 2 g of ethyl acetate. Analysis of the liquid product after 2 h showed an ethyl acetate conversion of 64% to methyl acetate.

COMPARATIVE EXAMPLE A

Example 12 was repeated in the absence of methyl acrylate. Analysis of the liquid product indicated that no reaction had occurred.

EXAMPLE 13

Transesterification of ethyl acetate to methyl acetate

Example 12 was repeated except that 0.7 g of bis(diphenylphosphino)ethane was used in place of tributylphosphine. Analysis of the liquid product showed an ethyl acetate conversion of 30% to methyl acetate.

EXAMPLE 14

Transesterification of ethyl acetate to methyl acetate

Example 12 was repeated except that 1.4 g of triphenyl phosphine was used in place of tributylphosphine, the amount of methyl acrylate used was increased to 1 g, and the reaction time for the transesterification stage increased to 24 hours. Analysis of the liquid product showed an ethyl acetate conversion of 30% to methyl acetate.

COMPARATIVE EXAMPLE B

Example 14 was repeated in the absence of triphenylphosphine. Analysis of the liquid product indicated that no reaction had taken place.

COMPARATIVE EXAMPLE C

Example 14 was repeated in the absence of methyl acrylate. Analysis of the liquid product indicated that no reaction had taken place.

EXAMPLE 16

Transesterification of propylene carbonate to dimethyl carbonate

Example 1 was repeated except that 2 g of propylene carbonate was used in place of ethyl acetate. Analysis of the liquid product showed a propylene carbonate conversion of 28% to dimethyl carbonate.

COMPARATIVE EXAMPLE D

Example 15 was repeated in the absence of ethyl acrylate. Analysis of the liquid product indicated that no reaction had taken place.

EXAMPLE 17

Carbonylation of methanol to methyl formate

A 100 ml high pressure stirred autoclave was charged with 30 g of methanol, 1 g of tributyl phosphine, and 1.5 g of acrylamide. The autoclave was sealed and flushed twice with carbon monoxide, following which it was pressurised to 50 bar with carbon monoxide and finally heated to 100° C. with stirring (1200 rpm). Rapid gas absorption occurred and the pressure was maintained between 49 and 56 bar by replenishment from a cylinder. After 3 hours gas absorption had ceased and the autoclave was cooled to 10° C. Analysis of the liquid product by gas chromatography showed a methanol conversion of 14% to methyl formate.

EXAMPLE 18

Carbonylation of methanol to methyl formate

Example 16 was repeated except that 1 g of methyl methacrylate was used as a promoter in place of acrylamide and the reaction was carried out at 120° C. Analysis of the liquid product showed a methanol conversion of 10% to methyl formate.

EXAMPLE 19

Carbonylation of methanol and diethylamine to methyl formate and diethyl formamide The autoclave described in Example 16 was charged with 26 g of methanol, 1 g of ethyl acrylate, 1 g of tributylphosphine, and 8.5 g of diethylamine. The autoclave was sealed and flushed twice with carbon monoxide, following which it was pressurised to 50 bar with carbon monoxide and finally heated to 80° C. with stirring (1250 rpm) for 6 hours. Analysis of the liquid product showed that all the diethylamine had been converted to diethyl formamide, and that 7% of the methanol has been converted to methyl formate.

EXAMPLE 20

Carbonylation of methanol and n-butylamine to methyl formate and n-butyl formamide Example 19 was repeated except that 8.5 g of n-butylamine was used in place of diethylamine and the reaction time was reduced to 3 hours. Analysis of the liquid product showed a quantitative conversion of n-butylamine to n-butyl formamide (and an 8% conversion of methanol to methyl formate).

EXAMPLE 21

Preparation of the catalyst precursor 4 g of tributyl phosphine were added slowly to 4 g of ethyl acrylate with stirring. The mixture so prepared was the catalyst precursor.

EXAMPLE 22

Preparation of the catalyst

The catalyst precursor produced in Example 21 was added to 200 g of methanol to generate the catalyst.

I claim:

1. A catalyst essentially consisting of a catalyst precursor essentially consisting of (i) an organophosphorus-containing compound in which the phosphorus is trivalent, said compound (i) selected from the group consisting of a mono-, di- or trialkylphosphine in which each of the alkyl groups contains from one to ten carbon atoms, wherein the individual alkyl groups can all be the same or different, or wherein the phosphine may be a mono-, di- or triarylphosphine or a mixed phosphine containing both said alkyl and said aryl groups and (ii) a compound which is reactable with the organophosphorus-containing compound and contains both (a) a double or triple bond and (b) an electron withdrawing group, wherein the compound (ii) containing the double or triple bond and electron withdrawing group has the formula:

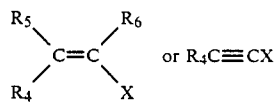

wherein X is an electron withdrawing group selected from —COOR, —COR, —CHO, —CON(R)$_2$, or —CN, where R is alkyl or aryl and where R$_4$, R$_5$ and R$_6$ are hydrogen or monovalent hydrocarbyl groups, and wherein the ratio of organophosphorus compound to the compound containing a double or triple bond and an electron withdrawing group is between 10:1 and 1:10 atoms of phosphorus per double or triple bond, and (iii) an alcohol or a mixture of an alcohol and a solvent.

2. A catalyst as claimed in claim 1 characterised in that the electron withdrawing group is selected from a carboxylic acid ester, ketone, aldehyde, amide and cyanide.

3. A catalyst as claimed in claim 1 characterised in that said ratio is between 2:1 and 1:2.

4. A catalyst as claimed in claim 1 characterised in that the alcohol is a lower aliphatic alcohol.

5. A catalyst as claimed in claim 1 characterised in that the organophosphorus-containing compound is bonded to an inert solid support.

6. A catalyst as claimed in claim 1, wherein the compound (ii) is selected from the group consisting of ethyl acrylate, acrylamide, methyl propiolate, methyl vinyl ketone, acrylonitrile, ethyl crotonate, methyl acrylate, and methyl methacrylate.

7. A catalyst as claimed in claim 1, wherein the molar ratio of phosphorus to alcohol is in the range 2:1 to 1:10,000.

8. A catalyst as claimed in claim 1, wherein the compound (ii) is selected from the group consisting of ethyl acrylate, methyl methacrylate, methyl acrylate, acrylonitrile and acrolein.

* * * * *

UNITED STATES PATENT AND TRADEMARK OFFICE
CERTIFICATE OF CORRECTION

PATENT NO. : 4,753,912

DATED : June 28, 1988

INVENTOR(S) : Michael J. Green

It is certified that error appears in the above-identified patent and that said Letters Patent is hereby corrected as shown below:

Col. 3, lines 19 and 20, ..."n"-propanol and "n"- butanol should be underlined.

Col. 3, line 65, ... "n"-propylformamide should be underlined.

Col. 5, line 30 should read ... of 79% "to" methyl acetate.

Strike Claim 2 and have it read as follows:...

"2. A catalyst as claimed in claim 1 characterised in that the electron withdrawing group is selected from ethyl acrylate methyl methacrylate, methyl acrylate, acrylonitrile and acrolein."

Signed and Sealed this

Twenty-first Day of February, 1989

*Attest:*

DONALD J. QUIGG

*Attesting Officer*     *Commissioner of Patents and Trademarks*